United States Patent [19]

Beard et al.

[11] Patent Number: 5,556,996
[45] Date of Patent: Sep. 17, 1996

[54] OXIRANYLS DISUBSTITUTED WITH A PHENYL GROUP AND A SUBSTITUTED CHROMANYL OR TETRAHYDROQUINOLINYL GROUP HAVING RETINOID LIKE ACTIVITY

[75] Inventors: Richard L. Beard, Santa Ana Heights; Roshantha A. Chandraratna, Missio Viejo, both of Calif.

[73] Assignee: Allergan, Waco, Tex.

[21] Appl. No.: 366,174

[22] Filed: Dec. 29, 1994

[51] Int. Cl.⁶ ................... C07D 311/04; C07D 311/58
[52] U.S. Cl. ................ 549/407; 549/404; 549/408; 549/409
[58] Field of Search ................... 549/407, 408, 549/409, 404

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 562/473 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |

(List continued on next page.)

FOREIGN PATENT DOCUMENTS

| | | |
|---|---|---|
| 0098591 | 1/1984 | European Pat. Off. ...... C07D 333/54 |
| 0130795 | 1/1985 | European Pat. Off. ...... C07D 311/58 |
| 170105A | 2/1986 | European Pat. Off. . |
| 0176033 | 4/1986 | European Pat. Off. ...... C07D 261/18 |
| 0176032 | 4/1986 | European Pat. Off. ........ C07C 65/38 |
| 176034A | 4/1986 | European Pat. Off. ........ C07C 63/66 |
| 0253302 | 1/1988 | European Pat. Off. ...... C07D 213/16 |
| 0272921 | 6/1988 | European Pat. Off. ...... C07D 213/80 |
| 0284288 | 9/1988 | European Pat. Off. ...... C07D 401/04 |
| 0303915 | 2/1989 | European Pat. Off. ..... A61K 31/255 |
| 0315071 | 5/1989 | European Pat. Off. ........ C07C 63/66 |
| 0350846 | 1/1990 | European Pat. Off. ...... C07D 311/58 |
| 3316932 | 11/1983 | Germany ........ C07C 63/66 |
| 3524199 | 1/1986 | Germany ........ C07C 63/66 |
| 3602473 | 7/1987 | Germany ........ C07C 43/215 |
| 3708060 | 9/1987 | Germany ........ C07D 311/04 |
| 3715955 | 11/1987 | Germany ........ C07C 15/58 |

| | | | |
|---|---|---|---|
| 2190378 | 11/1987 | United Kingdom | C07C 39/21 |
| 85-00806 | 2/1985 | WIPO | A61K 31/00 |
| 85-04652 | 10/1985 | WIPO | A61K 31/19 |
| WO91-16051 | 10/1991 | WIPO | A61K 31/44 |
| WO9206948 | 4/1992 | WIPO | C07C 69/86 |

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978, pp. 358–360.

Conversion of Methyl Ketones into Terminal Acetylenes and (E)–Tri–substituted Olefins of Terpenoid Origin by Ei–ichi, Anthony O. King, and William L. Klima, *J. Org. Chem.*, 45, No. 12, 1980, pp. 2526–2528.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al., *Chem. Phar. Bull.* 33:404–407 (1985).

Kagechika et al., *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'–Diacyl–1,1'–biaryls. Regiocontrolled Protection of . . . by Mervic, et al, *J. Org. Chem.*, No. 45, pp. 4720–4725, 1980.

A Dopamine Receptor Model and Its Application in the Design of a New Class of Rigid Pyrrolo[2,3–g]isoquinoline Antipsychotics, Gary L. Olson, et al. *American Chemical Society*, 1981, vo. 24, No. 9, pp. 1026–1031.

6.2.3 Conformational Restriction, Williams, et al., *Drug Discovery and Development*, 1987, The Humana Press, pp. 54–55.

V. Retinoid Structure—Biological Activity Relationships, Chemistry and Biology of Synthetic Retinoids, pp. 324–356, 1990.

Davis et al. *J. Organometallic Chem.*, 387, (1990), pp. 381–390.

(List continued on next page.)

Primary Examiner—Ba Kim Trinh
Attorney, Agent, or Firm—Gabor L. Szekeres; Robert J. Baran; Martin A. Voet

[57] ABSTRACT

Compounds of the formula

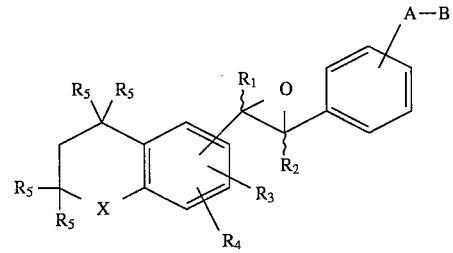

wherein all the symbols in the formula are as defined in the specification, have retinoid-like activity.

13 Claims, No Drawings

U.S. PATENT DOCUMENTS

| | | | |
|---|---|---|---|
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1993 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |

OTHER PUBLICATIONS

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology,* vol. 96, No. 5, May 1991, pp. 792–797.

Organ maintenance of human sebaceous glands: in vitro effects of 13–cis retinoic acid and testosterone, John Ridden, et al., Journal of Cell *Science,* Vo. 95, 1990, pp. 125–136.

Characterization of Human Sebaceous Cells In Vitro, Thomas I. Doran, et al., *The Journal of Investigative Dermatology,* vol. 96, No. 3, Mar. 1991.

Synthesis and Evaluation of Stilbene and Dihydrostilbene Derivatives as Potential Anticancer Agents That Inhibit Tubulin Polymerization by Cushman, Mark. et. al. *J.Med. Chem,* 1991, 34, 2579–2588.

Synthesis and Evaluation of New Protein–Tyrosine Kinase Inhibitors. Part 1. Pyridine–Containing Stilbenes and Amides by Cushman, Mark et al. *Bioorganic & Medicinal Chemistry Letters,* vol. 1, No.4, pp. 211–214, 1991.

Di–and Tri–methoxystyryl Derivatives of Heterocyclic Nitrogen Compounds by Bahner, C. T. et al. Arzneim–Forsch./Drug Res, 31 (I), Nr. 3 (1981).

Retinobenzoic acids. 3. Structure–Activity Relationships of retinoidal Azobenzene–4–carboxylic acids and Stilbene–4–carboxylic acids by H. Kagechika et al., *Journal of Medicinal Chemistry,* 1989, 32, pp. 1098–1108.

OXIRANYLS DISUBSTITUTED WITH A PHENYL GROUP AND A SUBSTITUTED CHROMANYL OR TETRAHYDROQUINOLINYL GROUP HAVING RETINOID LIKE ACTIVITY

BACKGROUND OF THE INVENTION

1. Field of the Invention

The present invention relates to novel compounds having retinoid-like activity. More specifically, the present invention relates to compounds having an oxiranyl phenyl carboxylic acid portion and a second portion which is a substituted or unsubstituted chromanyl, thiochromanyl or tetrahydroquinolinyl group. The acid function may also be converted to an alcohol, aldehyde or ketone or derivatives thereof, or may be reduced to —$CH_3$.

2. Background Art

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

European Patent EP 170 105 A discloses certain new para substituted 4-oxiranyl benzoic acids and their esters and amides having anti-cancer and anti-leukemia activity. The compounds are said to induce differentiation of pre-malignant and malignant cells, and therefore may serve in the therapy of pre-malignant and malignant diseases of humans and animals. An example of the compounds of this disclosure is benzoic acid, 4-[3-methyl-3-(5,6,7,8-tetrahydro-5,5,8,8-tetramethyl-2-naphthalenyl)oxiranyl-, trans-.

The article "Retinobenzoic acids. 3. Structure-Activity Relationships of retinoidal Azobenzene-4-carboxylic acids and Stilbene-4-carboxylic acids" by H. Kagechika et al., Journal of Medicinal Chemistry, 1989, 32, pp 1098–1108 discloses oxirans substituted with a 4-(carboxy)phenyl group and with 5,5,8,8-tetramethyltetrahydronaphthyl group.

U.S. Pat. No. 4,826,984 describes ethylene compounds substituted with a chromanyl or thiochromanyl group and with a substituted phenyl group as anticancer agents. Specific examples of this reference are ethyl (E)-p-[2-(4,-dimethylthiochroman-6-yl)propenyl]benzoate, and (E)-p-[2-(4,-dimethylthiochroman-6-yl)propenyl]benzoate.

Published German patent application DE 3316932 A1 also describes ethylene compounds substituted with a chromanyl or thiochromanyl group and with a substituted phenyl group. The compounds are described as active against acne, psoriasis and other dermatological disorders. Published European patent application Nos. 0 130 795 and 0 350 846 describe similar compounds.

International Application published under the Patent Cooperation Treaty WO 85/00806 describes ethylene compounds substituted with a chromanyl or thiochromanyl group and with a substituted heteroaryl group (such as pyridyl, pyrimidinyl and thienyl) as retinoid analogs.

Several co-pending applications and recently issued patents of the present inventor, which are assigned to the assignee of the present application, are directed to further compounds having retinoid like activity. One of said patents, U.S. Pat. No. 5,324,840, describes 2,2,4,4-tetramethyl-chroman-6-yl and phenyl substituted ethene derivatives where the chroman group also bears a substituent (such as an alkyl group) in the 7-position. Tetrahydronaphthyl and heteroaryl substituted ethene derivatives are further described in published European application EPO 0 098591, 0 253 302, and in published international application WO 92/06948.

SUMMARY OF THE INVENTION

The present invention covers compounds of Formula 1

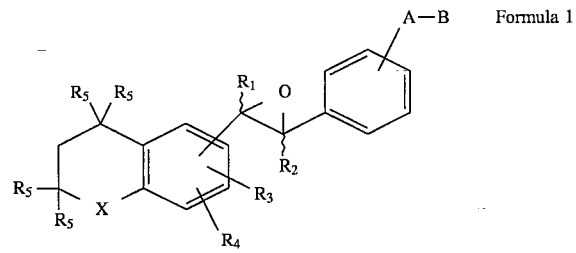

wherein X is O, NH or NR' where R' is lower alkyl;

$R_1$–$R_2$ are hydrogen, lower alkyl of 1 to 6 carbons, or halogen;

$R_3$ is hydrogen, lower alkyl of 1 to 6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$, $Si(R_{11})_3$;

$R_4$ is hydrogen, lower alkyl of 1 to 6 carbons, halogen, lower alkoxy or lower thioalkoxy of 1 to 6 carbons;

$R_5$ is independently hydrogen or lower alkyl of 1 to 6 carbons, and the oxiranyl ring is attached to the otherwise unoccupied 6 or 7 position of the chroman, thiochroman or tetrahydroquinoline nucleus;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl having 1 to 5 carbons, a cycloalkyl having 3 to 5 carbons or an alkenyl having 2 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

In a second aspect, this invention relates to the use of the compounds of Formula 1 as regulators for cell proliferation and differentiation, and particularly as agents for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointiural hyperproliferation, for treating and preventing other non-malignant hyperproliferative diseases such as endometrial hyperplasia, benign prostatic hypertrophy, proliferative vitreal retirropathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with dimethyl dioxirane, or with other reagent suitable for forming an oxirane (epoxide) ring from an ethene function.

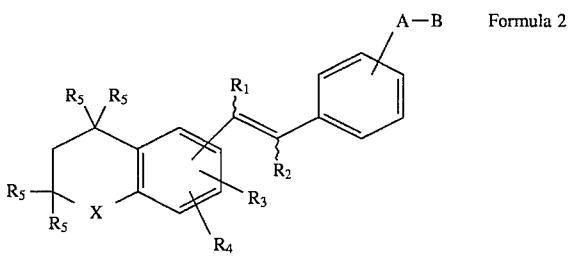

Formula 2 where $R_1$, $R_2$, $R_3$, $R_4$, $R_5$ and X are described above, A is the same as defined above; and B is H, or a protected acid, alcohol, aldehyde, or ketone, giving the corresponding compound of Formula 1. Still further, the present invention relates to such reactions performed on the compounds of Formula 1 which cause transformations of the A—B group while the reaction product still remains within the scope of Formula 1, that is without destroying the oxirane (epoxide) function.

GENERAL EMBODIMENTS

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 5 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming such-salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds utilized in accordance with the present invention have trans and cis (E and Z) isomers. In addition, the compounds of the present invention contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

In the preferred compounds of the invention the chromanyl, thiochromanyl or tetrahydroquinolinyl groups on the one hand and the phenyl groups on the other, are disposed in trans configuration about the oxirane ring. Compounds are also preferred where the oxiranyl group is in the 6 position of the chroman, thichroman or tetrahydroquinolin nucleus. Still further, compounds of the invention are preferred where the phenyl group is 1,4 (para) substituted.

With regard to the side chain (substituent) on the phenyl group, compounds are preferred where A is $(CH_2)_n$ and n is 0; and B is —COOH, an alkali metal salt or organic amine salt, or a lower alkyl ester therof, or —$CH_2OH$ and the lower alkyl esters and ethers thereof, (formed with a lower alkanoic acid or with a lower alkanol) or —CHO and acetal derivatives thereof. The $R_5$ groups are preferably methyl, $R_4$ is preferably hydrogen, and $R_3$ is preferably lower alkyl or hydrogen. $R_1$ is preferred as methyl, and $R_2$ as hydrogen. The most preferred compounds are shown in Formula 3:

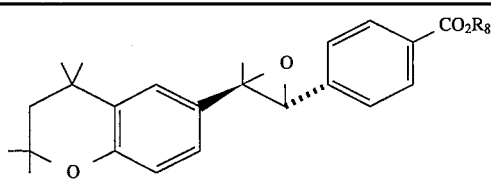

Formula 3

| Compound # | $R_8$ |
|---|---|
| 1 | $CH_3CH_2$ |
| 2 | H |

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Penna. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many disease for which these compounds are useful.

The retinoic acid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Re: 1662–1670,1975 may be used to demonstrate inhibition of TPA induction of ODC by compounds of this invention. Activity of exemplary compounds of the present invention in the above-described ODC assay is disclosed in Table 1 which provides $IC_{80}$ data for the exemplary compounds. ("$IC_{80}$" is that concentration of the test compound which causes 80% inhibition in the ODC assay).

TABLE 1

| Compound # | $IC_{80}$ conc (nmols) |
|---|---|
| 1 | >300 |
| 2 | 73 |

SPECIFIC EMBODIMENTS

The compounds of this invention can be made by the synthetic chemical pathways illustrated here. The synthetic chemist will readily appreciate that the conditions set out here are specific embodiments which can be generalized to any and all of the compounds represented by Formula 1.

Reaction Scheme 1

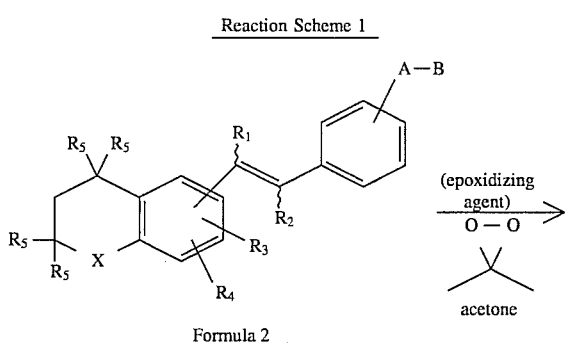

Formula 2

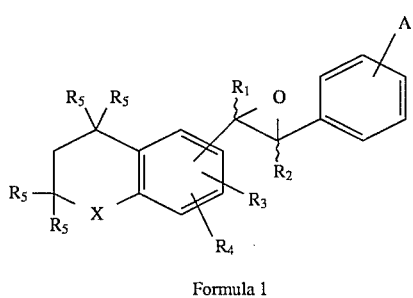

Formula 1

In accordance with Reaction Scheme 1, an olefin compound of Formula 2 is reacted with an oxidizing (epoxidizing) reagent which causes the formation of an oxirane (epoxide) ring from the "ethene" function of of the compounds of Formula 2. Examples of "epoxidizing" reagents suitable for this purpose are dimethyldioxirane, metachloroperoxy benzoic acid (MCPBA) and magnesium monoperoxy phthalate (MMPP). The use of dimethyldioxirane reagent for the reaction depicted in Reaction Scheme 1 is, however, preferred. The epoxidizing reaction with this reagent is typically conducted in an inert solvent, such as a halogenated hydrocarbon, an ether type solvent or acetone at room temperature for several hours, the reaction with dimethyldioxirane in methylene chloride ($CH_2Cl_2$) at room temperature for a duration of approximately 1 to 3 hours being particularly preferred. The reaction product is typically isolated and purified by chromatography on silica gel and or crystallization. When the starting olefin compound of Formula 2 is trans, the resulting oxirane is usually also of trans configuration. In Reaction Scheme 1 and in all other reaction schemes in the present description unless it is otherwise stated the symbols are defined as in connection with Formula 1.

The compounds obtained in accordance with Reaction Scheme 1 are typically the desired or target compounds in accordance with the present invention, or a protected or blocked derivative thereof. Certain chemical reactions of such nature (such as saponication of an ester under mild conditions, or removal of a mildly acid labile protecting group) which do not effect the oxirane (epoxide) ring may be performed on the compounds of Formula 1 to obtain still further compounds within the scope of the invention, or to remove a protecting or blocking group.

As it can be seen from the foregoing in accordance with Reaction Scheme 1, the "ethene" compounds of Formula 2 serve as starting materials for the synthesis of the compounds of the present invention. The ethene compounds of Formula 2 can be obtained by Wittig or analogous reactions, such as a Horner-Emmons reaction, in accordance with known procedures. Specifically, referring now to Reaction Scheme 2, and focusing attention to the exemplary compounds of the invention where the 6 position of the choman or tetrahydroquinolin nucleus is attached to the oxiranyl ring, the ethene compounds of Formula 7 can be obtained by a Horner-Emmons reaction between the ketone compound of Formula 5 and the phosphonate of Formula 6 in accordance with the teachings of U.S. Pat. No. 5,324,840, the entire specification of which is expressly incorporated herein by reference. The Horner-Emmons reaction is typically conducted in an ether type inert solvent, such as tetrahydrofuran, in the presence of strong base, such as potassium bis(trimethylsilyl)amide. (The compounds of Formula 7 differ from compounds of Formula 2 in that in Formula 7 the chroman or tetrahydroquinoline nucleus is substituted in the 6 position with the oxiranyl group, whereas in the compounds of Formula 2 such substitution can occur in the 6 or 7 position.)

The "ketone" compound of Formula 5 can be obtained in accordance with the teachings of U.S. Pat. No. 5,023,341 (Chandraratna) with a Friedel-Crafts reaction from the corresponding chroman or tetrahydroquinoline compound or Formula 4. The entire specification of U.S. Pat. No. 5,023,341 is incorporated herein by reference. Specifically, Reaction Schemes 5 and 6 of the '341 patent disclose the synthesis of the "ketone" compound where X of instant Formula 1 is oxygen, and Reaction Scheme 7 of the '341 patent discloses the synthesis of the "ketone" compound where X of instant Formula 1 is NH.

Reaction Scheme 2

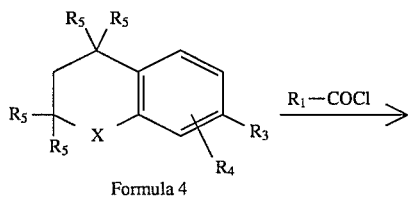

Formula 4

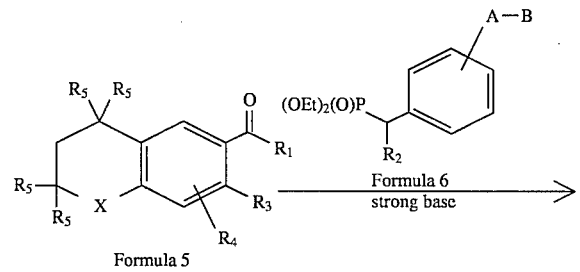

Formula 5

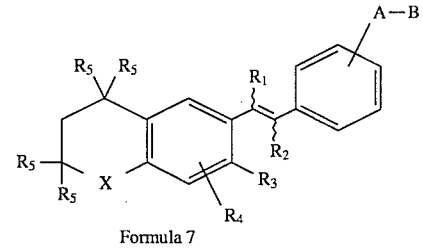

Formula 7

Reaction Scheme 3 summarizes another known method for synthesizing the olefin compounds of Formula 7, in accordance with the teachings of U.S. Pat. No. 4,826,984 (Berlin et al.), the specification of which is expressly incorporated herein by reference. In accordance with this patent, the ketone compound of Formula 5 is first reduced with a suitable reducing agent such as $LiAlH_4$, to provide the corresponding alcohol of Formula 8. The alcohol is therafter converted into the triphenylphosphonium salt of Formula 9 by treatment with triphenylphosphine hydrobromide in a suitable solvent such as methanol. The triphenylphosphonium salt of Formula 9 is reacted in a Wittig reaction (under Wittig conditions, i.e. in the presence of strong base) with an aromatic aldehyde or ketone of Formula 10) to yield the ethene compounds of Formula 7. The reference U.S. Pat. No. 5,324,840 discloses actual experimental procedures for the synthesis of ethyl (E)-4-[2-(2,2,4,4,7-pentamethylchroman- 6-yl)propen-1-yl]benzoate (and the corresponding carboxylic acid) in accordance with the above-summarized Reaction Scheme 2.

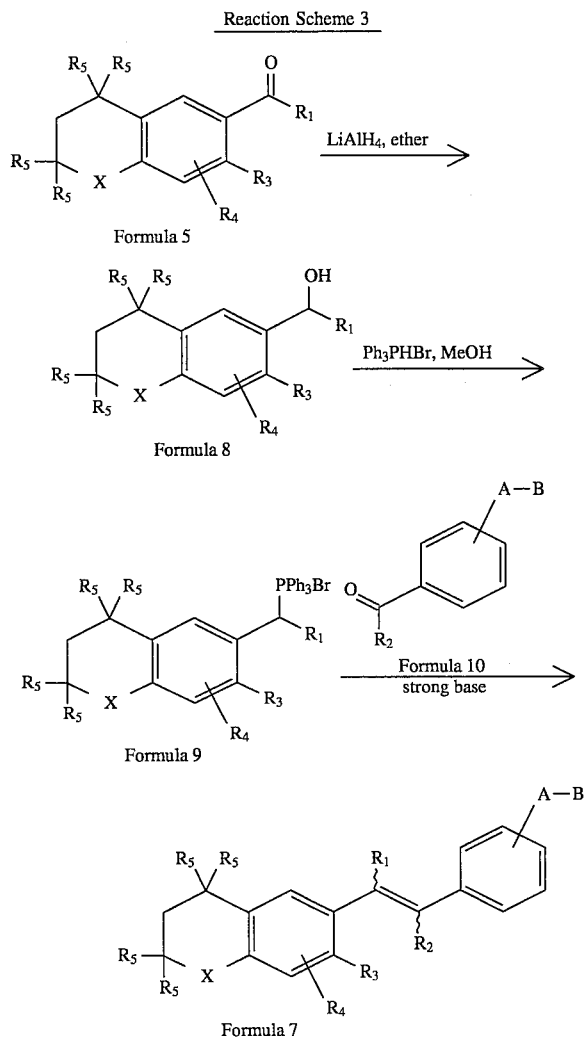

Reaction Scheme 3

Formula 5

Formula 8

Formula 9

Formula 7

Typically, the reagents of Formula 6 in Scheme 2 and of Formula 10 in Scheme 3 have an ester functionality (B is $COOR_8$), but it should be understood that analogous phosphonate reagents can, generally speaking, carry other A—B functionality, as such functionality is defined in connection with Formula 1.

The compounds of Formula 1 and particularly the compounds of Formula 2 which do not have the relatively reactive oxirane (epoxide) function, may be subjected to further transformations, particularly as far as synthetic tranformation of the A—B, and more particularly of the $COOR_8$ group, is concerned. In this regard, the following further well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before affecting the Horner-Emmons, (or analogous) coupling reaction of Reaction Scheme 2 (where such compounds corresponding to Formula 6 are not available from a commercial source) heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

An alternative means for making compounds where A is $(CH_2)_n$ (n is 1–5) is to subject the compounds of Formula 2, where B is an acid or other function, to homologation, using the Arndt-Eistert method referred to above, or other homologation procedures.

Compounds of Formula 2, where A is an alkenyl group having one or more double bonds can be made for example, by having the requisite number of double bonds incorporated into the intermediate which is coupled as a phosphonate with the ketone of Formula 5. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 2 where the A group has a triple (acetylenic) bond can be made by using the corresponding phosphonate intermediate. Such intermediate can be obtained by reactions well known in the art, for example, by reaction of a corresponding aromatic-methyl ketone with strong base, such as lithium diisopropyl amide. Double or triple bonds in the "side chain" A may, however, need to be protected in the epoxidation reaction of Scheme 1.

The acids and salts derived from compounds of Formula 2 are readily obtainable from the corresponding esters. Basic saponification with an alkali metal base will provide the acid. For example, an ester of Formula 2 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 2 where B is H can be prepared from the corresponding halogenated hetero aromatic compounds, preferably where the halogen is I.

Examples of reagents to be used in the Horner-Emmons type reaction of Reaction Scheme 2 to yield compounds of Formula 7 (from which the compounds of the invention of Formula 1 can be made by oxidation) are:

Diethyl (4-carboethoxybenzyl)phosphonate;
Diethyl (3-carboethoxybenzyl)phosphonate;
Diethyl (2-carboethoxybenzyl)phosphonate;
4,4-dimethyl-6-acetylchroman (U.S. Pat. No. 5,023,341);
2,2,4,4-tetramethyl-6-acetylchroman (U.S. Pat. No. 5,023,341);
2,2,4,4,7-pentamethyl-6-acetylchroman (U.S. Pat. No. 5,023,341).

Compounds of the invention where the chroman or tetrahydroquinoline nucleus is substitued in its 7-position with the oxiranyl ring can be made by oxidation from the corresponding "ethene" compounds. These in turn can be made by Horner-Emmons or Wittig reactions starting with the "ketone" compounds analogous in structure to Formula 5 but differing therefrom in that the 7 position of a chroman or tetrahydroquinoline derivative is substituted with a CO-R$_1$ group.

SPECIFIC EXAMPLES

4-Carboethoxybenzyl Bromide

To a stirred solution of 16.09 g (78 mmol) of 1,3-dicyclohexylcarbodiimide (Aldrich) in 100 ml methylene chloride was added a suspension of 15.4 g (71 mmol) of 4-carboxybenzyl bromide in 100 ml methylene chloride and then 4.9 g (106.5 mmol) of absolute ethanol and 0.81 g (7.1 mmol) of 4-dimethylaminopyridine. A further 50 ml of methylene chloride was added to the reaction mixture and mixture heated at reflux for 2 hours. The mixture was allowed to cool to room temperature and the resultant white precipitate removed by filtration. The filtrate was washed with water, dried (MgSO$_4$) and then concentrated in-vacuo to give the title compound as a colorless oil which crystallized on standing. PMR (CDCl$_3$); δ 1.39 (3H, t, J~7.2 Hz), 4.38 (2H, q, J~7.2 Hz), 4.50 (2H, s), 7.45 (2H, d, J~7.7 Hz), 8.03 (2H, d, J~7.7 Hz).

Ethyl 4-[(diethoxyphosphinyl)methyl]benzoate

A mixture of 11.8 g (48 mmol) of 4-carboethoxybenzyl bromide and 12.0 g (72 mmol) of freshly distilled triethylphosphite was placed in a flask fitted with an argon inlet and a dry-ice cooled trap. A continuous stream of argon was passed over the stirred reaction mixture and mixture heated at 120–° C. for 3 hours at which time no further ethyl bromide was being formed. The residue was purified by vacuum distillation to give the title compound as a colorless oil, BP=170°/0.35 mm). PMR (CDCl$_3$): δ 1.23 (6H, t, J~7.1 Hz), 1.39 (3H, t, J~6.9 Hz), 3.21 (2H, d, J~22.1 Hz), 4.02 (4H, m), 4.37 (2H, q, J~7.5 Hz), 7.38 (2H, d, J~7.9 Hz), 8.00 (2H, d, J~7.9 Hz).

4-[(E)-2-(2,2,4,4,7-pentamethylchromanyl-6-yl)propen-1-yl]-benzoate

A mixture of 3.25 g (10.8 mmol) of ethyl 4-[(diethoxyphosphinyl)methyl]benzoate and 7.7 mL (10.8 mmol) of 1.4M potassium bis(trimethylsilyl)amide in tetrahydrofuran (THF) was stirred for 30 minutes at room temperature under argon. A solution of 1.33 g (5.4 mmol) of methyl 2,2,4,4,7-pentamethylchroman-6-yl ketone also known as 2,2,4,4,7-pentamethyl-6-acetylchroman in 20 ml of DMSO was added and the resulting mixture stirred for 22 hours. To this was added 4.3 mL (8.6 mmol) of 2M sodium ethoxide and the mixture stirred an additional 2 hours. Sodium bicarbonate was then added and the mixture extracted with ether. The ether layer was washed with brine and dried (MgSO4). The solvent was removed in-vacuo and the resulting residue purified using flash chromatography (SiO2, 2% ethyl acetate in hexanes) to give a mixture of isomers which were separated using HPLC (1% ethyl acetate in hexanes) to give the title compound as a clear oil. PMR(0.1% ethylbenzene in CDCl$_3$): d 1.37 (6H, s), 1.38 (6H, s), 1.42 (3H, t), 1.84 (2H, s), 2.21 (3H, s), 2.28 (3H, s), 4.41(2H, q), 6.41(1H, s), 6.67 (1H, s), 7.10 (1H, s), 7.45 (2H, d, J~8.2 Hz), 8.06(2H, d, J~8.2 Hz).

4-[(E) -2-(2.2,4.4,7-pentamethylchromanyl-6-yl)propen-1-yl]-benzoic Acid

A solution of potassium hydroxide in ethanol was added to ethyl 4-[(E)-2-(2,2,4,4,7-pentamethylchromanyl-6-yl) propen-1-yl]benzoate and the resulting mixture stirred at room temperature. Solvent was removed in-vacuo and the resulting solid taken-up in water, acidified using 1N HCl, and extracted three times with ether. The ether extracts were washed with water, brine and dried (MgSO4). The solvent was removed in-vacuo to give the title compound as a pale yellow solid. PMR(d6-DMSO): d 1.38 (12H, s), 1.87 (2H, s), 2.23 (3H, s), 2.29 (3H, s), 6.44 (1H, s), 6.68 (1H, s), 7.10

(1H, s), 7.50 (2H, d, J~8.3 Hz), 8.14 (2H, d, J~8.3 Hz).

Ethyl 4-[(E)-2-(2,2,4,4-tetramethylchromanyl-6-yl)propen-1-yl]benzoate

A mixture of 2.6 g (8.6 mmol) of ethyl 4-[(diethoxyphosphinyl)methyl]benzoate and 6.0 mL (8.6 mmol) of 1.4M potassium bis(trimethylsilyl)amide in tetrahydrofuran (THF) was stirred for 30 minutes at room temperature under argon. A solution of 1.0 g (4.3 mmol) of methyl 2,2,4,4-tetramethylchroman-6-yl ketone, also known as 2,2,4,4-tetramethyl-6-acetylchroman, in 15 ml of DMSO was added and the resulting mixture stirred for 20 hours. To this was added 4.3 mL (8.6 mmol) of 2M sodium ethoxide and the mixture stirred an additional 2 hours. Sodium bicarbonate was then added and the mixture extracted with ether. The ether layer was washed with brine and dried (MgSO4). The solvent was removed in-vacuo and the resulting residue purified using flash chromatography (SiO$_2$, 2% ethyl acetate in hexanes) to give a mixture of isomers which were separated using HPLC (1% ethyl acetate in hexanes) to give the title compound as a clear oil. PMR(CDCl$_3$): 1.40(15H, m), 1.89(2H,s), 2.30(3H,s), 4.41(2H,q), 6.80(1H,s), 6.83(1H,d, J~8.7 Hz), 7.31(1H,dd,J~8.7 Hz, J~2.3 Hz), 7.44(2H,d,J~8.3 Hz), 7.46(1H,d,J~2.3 Hz), 8.06 (2H, d,J~8.3 Hz).

4-[(E)-2-(2,2,4,4-tetramethylchromanyl-6-yl)propen-1-yl]benzoic Acid

A solution of 5 mL of potassium hydroxide in ethanol was added to 0.350 g (0.926 mmol) of ethyl 4-[(E)-2-(2,2,4,4-tetramethylchromanyl-6-yl)propen-1-yl]benzoate and the resulting mixture stirred at room temperature for 48 hours. Solvent was removed in-vacuo and the resulting solid taken-up in water, acidified using 1N HCl, and extracted with ether. The ether extracts were washed with water, brine and dried (MgSO4). The solvent was removed in-vacuo to give the title compound as a pale yellow solid. PMR(CDCl$_3$): 1.41(6H,s), 1.43(6H,s), 1.90(2H,s), 2.33(3H,s), 6.85(2H,m), 7.32(1H,dd,J~8.3 Hz, J~2.3 Hz), 7.48(1H,d,J~2.3 Hz), 7.50(2H,d,J~8.3 Hz), 8.15(2H,d,J~8.3 Hz).

Ethyl(±)-(E)-4-[2-methyl-2-(2,2,4,4-tetramethylchroman-6-yl)oxiran-1-yl]benzoate (Compound 1)

To a solution of ethyl (E)-4-[2-(2,2,4,4-tetramethylchroman- 6-yl) propen-1-yl]benzoate (0.065 g, 0.17 mmol) in CH$_2$Cl$_2$ (3.0 ml) was added dimethyldioxirane (4.0 ml, 0.40 mmol, approx. 0.1M in acetone) and the resulting solution stirred at room temperature for 1.5 hours. Dimethylsulfide (0.15 ml, 0.13 g, 2.0 mmol) was added and the solution concentrated to give an oil. The oil was purified by flash column chromatography (SiO$_2$, 5% EtOAc/hexanes) to give the product as a clear oil (60.6 mg). $^1$HNMR: (CDCl$_3$, 300 MHz) δ 8.06 (2H, d, J=8.5 Hz), 7.45 (2H, d, J=8.1 Hz), 7.34 (1H, d, J=2.3 Hz), 7.14 (1H, dd, J=8.5 & 2.3 Hz), 6.80 (1H, d, J=8.4 Hz), 4.38 (2H, q, J=7.1 Hz), 4.02 (1H, s), 1.85 (2H, s), 1.39 (18H, m).

(±)-(E)T4-[2-methyl-2-(2,2,4,4-tetramethylchroman-6-yl)oxiran-1-yl]benzoic acid (Compound 2)

To a solution of (E)-4-[2-(2,2,4,4-tetramethylchroman-6-yl) propen-1-yl]benzoic acid (0.025 g, 0.071 mmol ) in acetone (0.5 ml ) was added dimethyldioxirane (4.0 ml, 0.40 mmol, approx. 0.1M in acetone) and the resulting solution was left undisturbed at room temperature for 3 days. The solution was concentrated under reduced pressure and the residue purified by flash column chromatography (SiO$_2$, 50% ethyl acetate in hexane) to give the product as a white solid (15 mg). $^1$HNMR: (CDCl$_3$, 300 MHz) δ 7.79 (2H, d, J=8.4 Hz), 7.11–7.08 (4H, overlapping d's), 6.62 (1H, d) J=8.4 Hz), 4.80 (1H, s), 1.46 (3H, s), 1.29 (6H, s), 1.18 (3H, s), 1.15 (3H, s).

What is claimed is:

1. A compound of the formula

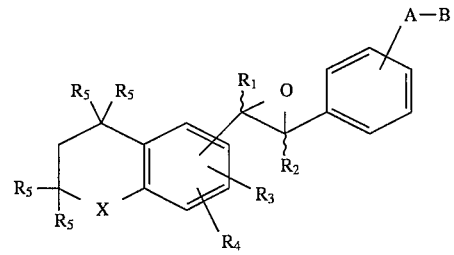

wherein X is O;

R$_1$ and R$_2$ independently are hydrogen, lower alkyl of 1 to 6 carbons, or halogen;

R$_3$ is hydrogen, lower alkyl of 1 to 6 carbons, halogen, OR$_{11}$, SR$_{11}$, OCOR$_{11}$, SCOR$_{11}$, NH$_2$, NHR$_{11}$, N(R$_{11}$)$_2$, NHCOR$_{11}$, or NR$_{11}$—COR$_{11}$, Si(R$_{11}$)$_3$;

R$_4$ is hydrogen, lower alkyl of 1 to 6 carbons, halogen, lower alkoxy or lower thioalkoxy of 1 to 6 carbons;

R$_5$ is independently hydrogen or lower alkyl of 1 to 6 carbons, and the oxiranyl ring is attached to the otherwise unoccupied 6 or 7 position of the chroman nucleus;

A is (CH$_2$)$_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl having 1 to 5 carbons, a cycloalkyl having 3 to 5 carbons or an alkenyl having 2 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

2. A compound of claim 1 where A is (CH$_2$)$_n$, n is 0 to 2, and B is COOH, COOR$_8$, or CONR$_9$R$_{10}$.

3. A compound of claim 1 where R$_3$ is methyl or hydrogen.

4. A compound of claim 1 where the heterocyclic group and the phenyl group are in trans configuration about the oxirane ring.

5. A compound of claim 1 where the oxiranyl group is attached to the 6-position of the heterocyclic group.

6. A compound of the formula

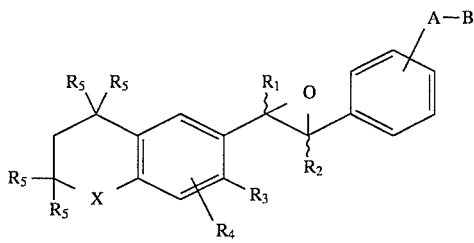

wherein X is O;

$R_1$, $R_2$, $R_3$ and $R_4$ independently are hydrogen, lower alkyl of 1 to 6 carbons, or halogen;

$R_5$ is hydrogen or lower alkyl of 1 to 6 carbons;

A is $(CH_2)_n$ where n is 0–5;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl having 1 to 5 carbons, a cycloalkyl having 3 to 5 carbons or an alkenyl having 2 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

7. A compound of claim 6 where n is 0 to 2, and B is COOH, $COOR_8$, or $CONR_9R_{10}$.

8. A compound of claim 7 wherein $R_1$ is hydrogen or methyl, $R_2$ is hydrogen, $R_3$ is hydrogen or methyl, $R_4$ is hydrogen, and $R_5$ is methyl.

9. A compound of the formula

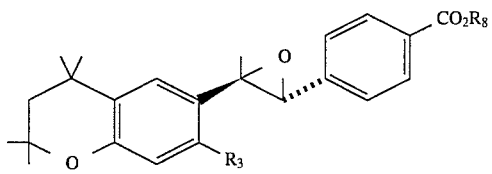

wherein $R_3$ is hydrogen or methyl, and $R_8$ is H, methyl or ethyl, or a pharmaceutically acceptable salt of said compound.

10. A compound of claim 9 wherein $R_3$ is $CH_3$.

11. A compound of claim 9 wherein $R_3$ is hydrogen.

12. The compound of claim 11 where $R_8$ is hydrogen, or a pharmaceutically acceptable salt of said compound.

13. The compound of claim 11 where $R_8$ is ethyl.

* * * * *

UNITED STATES PATENT AND TRADEMARK OFFICE
CERTIFICATE OF CORRECTION

PATENT NO. : 5,556,996
DATED      : September 17, 1996
INVENTOR(S): Beard et al.

It is certified that error appears in the above-indentified patent and that said Letters Patent is hereby corrected as shown below:

Column 7, line 30, please delete the second occurrence of "of";

Column 12, line 45, "SiO2" should be --$SiO_2$--;

Column 12, line 64; column 13, line 17 and column 13, line 38, "MgSO4" should be --$MgSO_4$--.

Column 13, line 60, "($\pm$)-(E)T4-" should be --($\pm$)-(E)-4- --.

Signed and Sealed this

Fifth Day of August, 1997

Attest:

BRUCE LEHMAN

Attesting Officer

Commissioner of Patents and Trademarks